United States Patent [19]

Bloch

[11] Patent Number: 5,972,618
[45] Date of Patent: Oct. 26, 1999

[54] DETECTION OF MUTATIONS IN NUCLEIC ACIDS BY CHEMICAL CLEAVAGE

[76] Inventor: Will Bloch, 850 Lincoln Center Dr., Foster City, Calif. 94404-1128

[21] Appl. No.: 09/130,258

[22] Filed: Aug. 6, 1998

Related U.S. Application Data

[63] Continuation-in-part of application No. 08/919,385, Aug. 28, 1997.

[51] Int. Cl.[6] .............. C12Q 1/68; C12P 19/34; C07H 21/02; C07H 21/04
[52] U.S. Cl. ............ 435/6; 435/91.2; 536/23.1; 536/24.3
[58] Field of Search .................. 435/5, 6, 91.2; 536/23.1, 24.3; 935/76, 77, 78

[56] References Cited

U.S. PATENT DOCUMENTS

| | | | |
|---|---|---|---|
| 4,818,268 | 4/1989 | Holtz | 71/5 |
| 5,217,863 | 6/1993 | Cotton et al. | 435/6 |

FOREIGN PATENT DOCUMENTS

| | | | |
|---|---|---|---|
| 0 329 311 | 8/1989 | European Pat. Off. | C12Q 1/68 |
| 0 507 591 | 10/1992 | European Pat. Off. | B01J 41/06 |
| WO 95/07361 | 3/1995 | WIPO | C12Q 1/68 |
| WO 97/12993 | 4/1997 | WIPO | C12Q 1/68 |

*Primary Examiner*—W. Gary. Jones
*Assistant Examiner*—Ethan Whisenant
*Attorney, Agent, or Firm*—Paul Grossman

[57] ABSTRACT

Improved methods, compositions and kits for detecting mutations in nucleic acids are disclosed, such comprise annealing a piece of control nucleic acid without mutations to a piece of test nucleic acid very similar in sequence to the control nucleic acid but possibly containing mutations, treating this mixture with potassium permanganate or hydroxylamine to remove mismatched bases from the duplex nucleic acid, treating the resulting nucleic acid with any of a class of diamines, triamines, and tetraamines analogous to 1,2-ethylenediamine to cleave abasic sites, and then analyzing the chemically treated nucleic acid to determine whether cleavage has occurred and approximately at what position in the nucleic acid any cleavage has occurred. Inclusion of betaine in the base-removal reactions improves their sensitivity and specificity. This series of non-hazardous, non-noxious, chemical treatments can be performed rapidly in a single reaction tube with no or minimal intervening separation steps; and the cleavage product can be prepared for the analysis step without removing the chemical reagents used to effect cleavage.

52 Claims, No Drawings

DETECTION OF MUTATIONS IN NUCLEIC ACIDS BY CHEMICAL CLEAVAGE

This application is a C-I-P of Ser. No. 08/919,385 filed Aug. 28, 1997.

FIELD OF THE INVENTION

This invention relates to the detection of mutations in nucleic acids. As such, it serves the fields of genetics, molecular biology, and medicine, being especially useful as an economical, first-stage, clinical diagnostic screen for mutations causing or predisposing for disease.

REFERENCES

Baskaran et al., *Genome Research*, 6:633–638 (1996)

Bloch, European Patent Application 0 507 591 A2 (1992)

Carmody and Vary, *BioTechniques*, 15:692–699 (1993)

Cotton et al., U.S. Pat. No. 5,217,863 (1993)

Dianzani et al., *American Journal of Human Genetics*, 48: 423–424 (1991)

Dieffenbach & Dveksler, *PCR Primer: A Laboratory Manual*, CSHL Press (1995)

Gogos et al., *Nucleic Acids Research*, 18: 6807–6814 (1990)

Maxam and Gilbert, *Methods in Enzymology*, 65, 499–560 (1980)

McHugh and Knowland, Nucleic Acids Research 23: 1664–1670 (1995)

Melchior and von Hippel, *Proceedings of the National Academy of Sciences U.S.A*, 70: 292–302 (1973)

Meo et al., WO95/07361 (1995)

Mytelka and Chamberlin, *Nucleic Acids Research*, 24(14): 2774–2781 (1996)

Papp et al., *Molecular Diagnosis*, 1: 59–64 (1996)

Ramus and Cotton, *BioTechniques*, 21, 216–220 (1996)

Rees et al., *Biochemistry*, 32:, 137–144 (1993)

Rubin and Schmid, *Nucleic Acids Research*, 8:4613–4619 (1980)

Shapiro et al, *Biochemistry*, 9:3233–3241 (1969)

Weissensteiner and Lanchbury, *BioTechniques*, 21:1102–1108 (1996)

BACKGROUND

Understanding the variation, or polymorphism, in a species's genome serves multiple scientific and practical goals. Examples include the study of evolutionary relatedness, the study of the genetic relatedness and geographical dispersion of populations within a species, the study of disease mechanism and predisposition, genetic linkage mapping in genome study and animal and plant breeding, the forensic identification and differentiation of individuals, the clinical diagnosis and prognosis of inherited diseases and cancer, and the clinical diagnosis and prognosis of drug resistance in infectious microorganisms.

A variety of methods have been described for discovering mutations, a process sometimes called "mutation scanning". Representative methods include denaturing gradient gel electrophoresis, constant denaturant gel electrophoresis, temporal temperature gradient gel electrophoresis, single-stranded conformational polymorphism analysis, denaturing HPLC, direct heteroduplex electrophoretic analysis, protein truncation test, immobilized mismatch binding protein assay, cleavage fragment length polymorphism analysis, enzymatic mismatch scanning, chemical cleavage of mismatch analysis (CCM), and complete sequence analysis (e.g., Sanger sequencing). As presently practiced, each of these methods suffers from one or more disadvantages which limits its value for cost-effective, high-throughput, reliable, mutation scanning, including low clinical specificity (a significant false-positive rate); low clinical sensitivity (a significant false-negative rate); low sensitivity to mutations present in only a small fraction of the nucleic acid (with a high normal background); limitation to relatively short sequences; low information content; low throughput; low potential for automation; high labor requirement; long turnaround time; dependence on expensive, labile, or proprietary reagents; or dependence on toxic or noxious reagents.

Of the mutation scanning methods listed above, CCM is one of the most attractive, especially for clinical applications requiring specificity, sensitivity, high information content, and low cost. However, conventional CCM methods (Cotton; Meo) suffer from two major weaknesses: (1) the use of toxic and noxious reagents and (2) the need for multiple, labor-intensive, hard-to-automate, technically demanding separation steps to remove the CCM reagents from the nucleic acid sample.

Conventional CCM entails the application of Maxam-Gilbert sequencing chemistry (Maxam and Gilbert) to the reactive mismatched bases generated when largely identical normal and mutant ("parental") sequences are mixed, denatured, and re-annealed to create a mixture of parental (perfectly matched) duplexes and heteroduplexes, where the heteroduplexes, containing one strand from each of the parental sequences, are mismatched at any mutant positions. There are two common ways to create heteroduplexes. (1) Nucleic acid samples purified from control and test individuals or tissues can be mixed, denatured by heating or adding alkali, and renatured by cooling or adding acid to return the pH approximately to neutrality. This method works whether the test sample is homozygous or heterozygous for the mutation. (2) Alternatively, as long as the test sample is likely to contain a mixture of normal and mutant sequences (e.g., because it is heterozygous for any mutation or because it is purified from a mixture of normal and mutant cells, as in many cancers), it can be denatured and renatured to form heteroduplex without adding control nucleic acid (Dianzani). The nucleic acid in question is almost always entirely DNA, but CCM is distinguished from some of the other mutation scanning methods in that one or both nucleic acid samples could be RNA. The parental nucleic acids could, in principle, be single-stranded, as long as the mixture contained the complementary strands needed to form a duplex molecule; but in practice the parental molecules are almost always duplex DNA, generated by PCR amplification of a sequence from genomic DNA or from cDNA generated from RNA by a reverse transcription reaction.

In conventional CCM, chemical treatment of potential heteroduplex to cleave at mismatched sites occurs in two stages. First, in a base-removal step, the nucleic acid is treated either (a) with moderately concentrated (16 mM) aqueous osmium tetroxide ($OsO_4$) in fairly concentrated (0.3 M) pyridine under conditions favoring destruction of mismatched thymines while minimally affecting matched base pairs and mismatched purines and cytosines, or (b) with concentrated (about 4 M) aqueous hydroxylamine ($NH_2OH$) in concentrated (about 2 M) diethylammonium chloride under conditions favoring destruction of mismatched cytosines, substantially sparing matched base pairs and mismatched purines and thymines. The two base-removal reactions are run separately, in parallel, in order to assure that all mutations are detected and to supply some information about the chemical nature of the mutation. Following the base-removal reaction, the base-removal reagent is separated from the nucleic acid, typically by ethanol precipitation. Next, in a cleavage reaction, concentrated (1 M) aqueous piperidine is incubated with the nucleic acid and incubated at about 90° C. for about 20 minutes to cleave any abasic sites generated by the base-removal reaction. Because the base-removal reaction usually removes only pyrimidines, cleavage commonly generates nicked duplex nucleic acid rather than double-stranded breaks. Then ethanol precipitation is used again, to eliminate the cleavage reagent, before dissolving the nucleic acid in a solvent suitable for subsequent analysis. Typically, analysis of the cleaved heteroduplex is performed by denaturing gel electrophoresis, in a high-resolution sequencing gel capable of detecting differences the size of the parental strands and any cleavage fragments to within one or a few nucleotides. Also typically, the nucleic acid strands are tagged at the 5' end with either radioactivity or fluorescent dyes, in a way which allows approximate or exact location of the cleavage point in the nucleic acid sequence. For example, one PCR primer is 5'-tagged with a fluorescent dye, the other primer is tagged with a rhodamine dye, and the cleavage product is analyzed on a multicolor, automated DNA sequencer (Meo). Any heteroduplex molecule with only one mismatched position can be cleaved on only the strand(s) containing a mismatched pyrimidine, but every heteroduplex population generated from duplex parental molecules must contain two, "complementary", mismatched heteroduplex molecules. Therefore, several different fluorescent electropherograms can be obtained for base-substitution mutations, depending on whether the mismatch pair is A—A and T—T, C—C and G—G, A-G and T-C, or A-C, and G-T, and on whether $OsO_4$ or $NH_2OH$ was used for mismatched pyrimidine removal. With two-dye fluorescent analysis, the position and chemical nature of the mutation can be determined from the two patterns obtained with the two base-removal reagents.

Informative though the conventional CCM method is, it is unsuitable for economical, high-throughput, clinical mutation screening. $OsO_4$ is volatile, toxic, and noxious; pyridine is volatile and noxious; $NH_2OH$ is volatile, putatively carcinogenic, and mildly noxious; and piperidine is volatile and noxious. This toxicology is aggravated by the high concentrations needed for effectiveness. Furthermore, the several nucleic acid precipitation and washing steps increase operator exposure to the undesirable reagents, require considerable operator skill and judgment to get good recoveries, and are difficult to automate. Finally, hot aqueous piperidine occasionally causes some background cleavage at sites where no base removal has occurred.

One published effort to reduce the operational complexity of conventional CCM effected mismatched cytosine and thymine removal serially on one sample rather than in parallel on two samples, but could not avoid the inclusion of a separation step after each chemical step (Ramus and Cotton). It was reported to be important to remove cytosine before thymine.

Gogos et al. showed that dilute (0.1 mM) potassium permanganate ($KMnO_4$, a non-noxious and effectively non-toxic reagent) could replace $OsO_4$/pyridine for mismatched thymine removal from heteroduplexes, with much improved sensitivity and specificity if the reaction occurred in 3 M tetramethylammonium chloride (TMAC) (Gogos). They also showed that 0.5 to 4 M tetraethylammonium chloride (TEAC) (2 M preferred) increased the sensitivity and specificity of mismatched cytidine removal by $NH_2OH$. They reduced the need for demanding separation steps by adsorbing the DNA to an ion-exchange paper, performing the chemical treatments on paper-bound DNA, and changing chemical conditions simply by shifting the paper from one reagent solution to another with an intervening water wash. Unfortunately, the commercial supplier of the ion-exchange paper (Amersham) since has discontinued its sale. Furthermore, the piperidine treatment removed the cleaved DNA from the paper, so that time-consuming lyophilization was needed to remove the concentrated piperidine from the DNA before electrophoretic analysis. In addition, Gogos et al. stated that their improved reagents were more specific (and therefore successful) for immobilized DNA than for DNA treated in solution. Another limitation of this work was that almost all experiments studied the cleavage of labeled oligonucleotide probes interrogating only rather short (approximately 30 nt) sequences: unrealistic models for the PCR-generated polynucleotide samples needed for cost-effective clinical mutation scanning.

In a totally different application not dependent on base-removal reagents (chemical detection of photoproducts in UV-damaged DNA), McHugh and Knowland showed that 1,2-ethylenediamine and two related compounds (piperazine and N,N'-dimethylethylenediamine) can replace piperidine for cleaving abasic sites in duplex DNA. These relatively non-toxic reagents generate cleavage products with subtle structural differences yielding observable electrophoretic mobility differences, but they have several striking advantages over piperidine which could greatly benefit mutation detection. (1) They are effective at much lower concentrations than piperidine (as low as 20 mM for ethylenediamine). (2) They cause much less background cleavage of perfectly matched duplex DNA than does piperidine.

The TMAC found by Gogos to improve $KMnO_4$ sensitivity and specificity may be crucial to this advance because of the documented binding to and stabilization of duplex DNA by tetramethylammonium ion (Shapiro; Melchior and von Hippel). The necessarily high concentration of TMAC, a strong electrolyte, should interfere with direct electrophoretic analysis because it increases conductivity of the electrophoresis sample by over an order of magnitude. It may also block the electrostatic interaction of ethylenediamine and its analogs with duplex DNA which was theorized by McHugh and Knowland to be responsible for their unusual cleavage efficiency.

Betaine, a zwitterionic analog of tetramethylammonium ion which has no net charge at pH values near and above neutrality, appears to affect duplex DNA stability much the same way that tetramethylammonium ion does (Rees). The benefit of high betaine concentrations already has been applied to the sequencing and PCR amplification of difficult, usually GC-rich, nucleic acid targets, where this additive improves the interaction of the DNA polymerase with its substrate (in some way not yet completely understood) without increasing the ionic strength to levels which would inhibit the enzyme (Papp; Mytelka and Chamberlin; Baskaran; Weissensteiner and Lanchbury).

The operational simplicity of the present invention derives significantly from finding chemical conditions where both pyrimidines (and even purines) are removed from mismatched positions while remaining substantially untouched in correctly matched duplex DNA. Uracil can be completely substituted for thymine in PCR with some reduction of amplification efficiency; radical reduction in the sensitivity of hybridization-based detection of dU-containing amplicon implies that replacement of T with dU significantly changes the conformation or stability of AT-rich sequences of duplex DNA (Carmody and Vary). It has been noted in sequencing applications, which examine single-stranded DNA, that although thymine resists hydroxylamine attack at all pH values, uracil can be removed by NH$_2$OH at high pH (Rubin and Schmid). This observation raises the question whether under appropriate conditions NH$_2$OH can function as a single reagent for removal of both mismatched C and U from duplex DNA. The technical challenge in improving mutation scanning by CCM is to optimize and streamline the use of chemistries developed to analyze single-stranded DNA in an application which preserves the structure and chemical inertia of perfectly matched regions of duplex DNA.

SUMMARY

The present invention is directed towards the discovery of improved methods, reagents and kits for performing mutation scanning by chemical cleavage of mismatched heteroduplex nucleic acid.

It is an object of the invention to minimize the number of steps required to perform a CCM process, in particular, to avoid separation steps.

It is another object of the invention to reduce the toxicity of reagents used in a CCM process.

It is yet another object of the invention to reduce the level of nonspecific cleavage in a cleavage reaction step of a CCM process.

It is another object of the invention to improve the speed, automatability and reliability of a CCM process.

It is yet another object of the invention to perform all chemical steps in only one or two reaction vessels with minimal liquid transfer of the nucleic acid.

A first aspect of the invention entails the use of potassium permanganate in the base-removal step of CCM, at a concentration and under conditions of time, temperature, and solvent composition effective to cause removal of mismatched thymines and cytosines in duplex nucleic acid substantially without removal of correctly matched bases. In a first embodiment, this aspect employs a base-removal solvent containing a tetraalkylammonium salt in the concentration range of approximately 1M to approximately 5M. The preferred alkyl groups of the tetraalkylammonium cation are methyl and ethyl. Many tetraalkyammonium salts are effective; the anion of the salt may be taken from the group consisting of chloride, fluoride, hydrogen sulfate, sulfate, nitrate, silicate, and tetrafluoroborate. In this embodiment, this reaction product is substantially desalted before the cleavage step, for example, by adding a 10- to 100-fold excess volume of water and subjecting the diluted mixture to diafiltration until approximately the original volume is obtained. To the desalted mixture is added a cleavage reagent, taken from the group consisting of 1,2-diamines, at a concentration effective for the cleavage of any abasic sites generated in the base-removal step, substantially without cleavage of normal phosphodiester bonds. After incubation at a pH between about 6 and about 9, at a temperature and for a time effective for cleavage of abasic sites, the cleavage mixture is diluted directly into the reagent used to prepare the sample for fragment size analysis. The group of 1,2-diamines comprises 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, and trans-1,2,-diaminocyclohexane. Because cleavage of abasic sites is much more efficient in single-stranded than in double-stranded nucleic acid, the cleavage reagent preferably is accompanied by a nucleic acid denaturant. Preferred denaturants are urea, formamide, dimethyl sulfoxide, and lactams, such as 2-pyrrolidinone and 1-methyl-2-pyrrolidinone. In this case, the thermal treatment for cleavage should include transient exposure to a temperature high enough to denature any duplex nucleic acid.

In a second, preferred, embodiment of the first aspect of the invention, no tetraalkylammonium salt is used during base removal; instead, the base-removal solvent contains betaine in the concentration range of approximately 1 M to 5 M. Alternatively, neither betaine nor tetraalkylammonium salt may be present during mismatched base removal. In this latter embodiment, the product of the base-removal step enters directly into the cleavage step, following addition of a cleavage reagent taken from the group consisting of 1,2-diamines, at a concentration effective for the cleavage of any abasic sites generated in the base-removal step, substantially without cleavage of normal phosphodiester bonds. After incubation at a pH between about 6 and about 9, at a temperature and for a time effective for cleavage of abasic sites, the cleavage mixture is diluted directly into the reagent used to prepare the sample for fragment size analysis. The cleavage reaction preferably is effected in the presence of nucleic acid denaturant at a concentration which renders the test nucleic acid substantially single-stranded.

A second, less preferred, aspect of the invention entails first the use of potassium permanganate in the base-removal step of CCM, at a concentration and under conditions of time, temperature, and solvent composition effective to cause removal primarily of mismatched thymines in duplex nucleic acid substantially without removal of correctly matched bases or mismatched cytidines, followed by addition to this reaction mixture of hydroxylamine in the presence of substantially no additional salt, at a pH between about 8 and about 10, and at a concentration effective for the removal of mismatched cytidines from duplex nucleic acid substantially without removal of correctly matched bases. In a first embodiment, this aspect employs a base-removal solvent containing a tetraalkylammonium salt in the concentration range of approximately 1 M to approximately 5 M. Many tetraalkylammonium salts are effective; the anion of the salt may be taken from the group consisting of chloride, fluoride, hydrogen sulfate, sulfate, nitrate, silicate, and tetrafluoroborate. In this embodiment, the base-removal product is substantially desalted before the cleavage step, for example, by adding a 10- to 100-fold excess volume of water and subjecting the diluted mixture to diafiltration until approximately the original volume is obtained. To the desalted mixture is added a cleavage reagent, taken from the group consisting of 1,2-diamines, at a concentration effective for the cleavage of any abasic sites generated in the base-removal step, substantially without cleavage of normal phosphodiester bonds. After incubation at a pH between about 6 and about 9, at a temperature and for a time effective for cleavage of abasic sites, the cleavage mixture is diluted directly into the reagent used to prepare the sample for fragment size analysis. The cleavage reaction preferably is effected in the presence of a nucleic acid denaturant at a concentration which renders the test nucleic acid substantially single-stranded.

In a second, preferred, embodiment of the second aspect of the invention, no tetramethylammonium salt is used during base removal; instead, the base-removal solvent contains betaine in the concentration range of approximately 1 M to 5 M. Alternatively, neither betaine nor a tetraalkylammonium salt may be present during mismatched base removal. In this latter embodiment, the product of the base-removal step enters directly into the cleavage step, following addition of a cleavage reagent, taken from the group consisting of 1,2-diamines, at a concentration effective for the cleavage of any abasic sites generated in the base-removal step, substantially without cleavage of normal phosphodiester bonds. After incubation at a pH between about 6 and about 9, at a temperature and for a time effective for cleavage of abasic sites, the cleavage mixture is diluted directly into the reagent used to prepare the sample for fragment size analysis. The cleavage reaction preferably is effected in the presence of a nucleic acid denaturant at a concentration which renders the test nucleic acid substantially single-stranded.

A third, preferred, aspect of the invention entails the use of dUTP instead of TTP in the PCR used to prepare samples for CCM analysis and the use of hydroxylamine in the base-removal step of CCM, at a concentration and under conditions of time, temperature, and solvent composition (including pH) effective to cause removal of mismatched uracils and cytosines in duplex DNA substantially without removal of correctly matched bases. The product of the base-removal step enters directly into the cleavage step, following addition of a cleavage reagent, taken from the group consisting of 1,2-diamines, at a concentration effective for the cleavage of any abasic sites generated in the base-removal step, substantially without cleavage of normal phosphodiester bonds. After incubation at a pH between about 6 and about 9, at a temperature and for a time effective for cleavage of abasic sites, the cleavage mixture is diluted directly into the reagent used to prepare the sample for fragment size analysis. The cleavage reaction preferably is effected in the presence of a nucleic acid denaturant at a concentration which renders the test nucleic acid substantially single-stranded. In an especially preferred embodiment of this aspect of the invention, the base-removal step of CCM occurs in the presence of betaine in the concentration range of about 1 M to about 5 M. In another preferred embodiment, the same approximate concentration of betaine is present during the PCR used to prepare samples for CCM analysis. A less preferred embodiment of this aspect of the invention employs a base-removal solvent containing a tetraalkylammonium salt in the concentration range of approximately 1 M to approximately 5 M, wherein the alkyl group is taken from the group consisting of ethyl and methyl. Many such tetraalkylammonium salts are effective; the anion of the salt may be taken from the group consisting of bromide, chloride, fluoride, hydrogen sulfate, sulfate, nitrate, acetate, formate, hydrogen phthalate, silicate, and tetrafluoroborate. In this embodiment, the base-removal product is substantially desalted before the cleavage step, for example, by adding a 10- to 100-fold excess volume of water and subjecting the diluted mixture to diafiltration until approximately the original volume is obtained.

The invention further comprises methods, compositions, and kits which incorporate and enable the various aspects and embodiments described above.

These and other objects, features, and advantages of the present invention will become better understood with reference to the following description, drawings, and appended claims.

DETAILED DESCRIPTION OF THE PREFERRED EMBODIMENTS

Reference will now be made in detail to the preferred embodiments of the invention. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, mutation scanning by chemical cleavage of mismatch (CCM) is a four-step process. First, normal and putatively mutated versions of the same general nucleic acid sequence, commonly prepared by PCR, are mixed, denatured, and renatured so that, if mutations are present, heteroduplex molecules will be formed which have mismatched bases at the mutated positions. Second, the heteroduplex nucleic acid is treated with a base-removal reagent which removes bases, commonly the pyrimidines, e.g., thymine and cytosine, from the mismatched positions in the heteroduplexes while sparing correctly matched bases. Such base removal results in an abasic site at that position. Third, the base-removal product is treated with a cleavage reagent which cleaves the heteroduplex at the abasic sites created in the base-removal reaction, preferably under conditions which render the treated heteroduplex substantially single-stranded. Finally, the cleavage product is analyzed, commonly by denaturing electrophoresis, to characterize the cleavage products produced in the cleavage reaction.

The success of various aspects and embodiments of the invention depends in part (1) on the surprising chemical compatibilities (a) of betaine with $KMnO_4$ and $NH_2OH$ removal of mismatched bases from heteroduplex nucleic acid, (b) of betaine with 1,2-diamine cleavage of abasic sites, (c) of $KMnO_4$ with $NH_2OH$ removal of mismatched cytosine, (d) of $KMnO_4$ and hydroxylamine with 1,2-diamine cleavage of abasic sites, (e) of nucleic acid denaturants such as 2-pyrrolidinone with 1,2-diamine cleavage of abasic sites, and (f) of $KMnO_4$, $NH_2OH$, betaine, and 1,2-diamines with electrophoretic separation; (2) on the discovery of chemical conditions where mismatched thymine (or uracil) and cytosine are removed from duplex nucleic acid with comparable efficiencies; and (3) on the surprising improvements in cleavage of abasic sites effected by certain members of the group of 1,2-diamines, especially under conditions wherein the nucleic acid has been rendered single-stranded.

I. DEFINITIONS

Unless stated otherwise, the following terms and phrases as used herein are intended to have the following meanings:

"1,2-diamine" means a molecule having the general structure

wherein (1) $R_1$ and $R_8$ are H atoms; (2) $R_{2-7}$ can be H atoms, alkyl groups, or aralkyl groups; (3) any single pair of $R_{2-7}$ can be covalently linked to form a ring composed of 5–10 atoms; (4) $R_2$ and $R_7$ can be alkyl groups wherein one or more methylene groups have been replaces with NH groups; (5) $R_2$ and $R_7$ can be alkyl groups wherein one or more methyl groups have been replaced with $NH_2$ groups; (7) $R_{2-7}$ can contain one or more carboxyl, carboxamide, or carboxylic ester groups; (8) the atoms in $R_2$ and $R_7$ immediately next to the indicated N atoms are either H atoms or C atoms bonded to a total of four other atoms; and (9) said molecule contains no aldehyde groups, ketone groups, or other groups with substantial covalent reactivity toward amino groups at temperatures below about 50C. For the purpose of the present invention, preferred 1,2-diamines are 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, and trans-1,2,-diaminocyclohexane.

"Nucleic acid denaturant" means a non-ionic, water-soluble, organic compound which, when added to an aqueous solution of nucleic acid, promotes the transformation of any duplex or triplex nucleic acid into single-stranded nucleic acid. The solution may be heated to a temperature in the approximate range of 50–100° C. to effect this transformation, or may be so treated and then rapidly cooled to approximately 25° C. or below. For the purpose of the invention, preferred nucleic acid denaturants are dimethyl sulfoxide, urea, formamide, or a lactam, applied separately or in combination. Preferred lactams are 2-pyrrolidinone and 1-methyl-2-pyrrolidinone.

II. TEST NUCLEIC ACID

Although the chemical basis of mutation scanning by chemical cleavage of mismatch (CCM) serves equally well for RNA and DNA, in practice the method is preferably applied to a DNA test nucleic acid because RNA is harder to obtain in sufficient quantity in stable form.

Preferably the test nucleic acid component of the nucleic acid sample is obtained through a polymerase chain reaction (PCR) which targets a sequence of about 100 to about 10,000 nucleotides in length. Most practically, the PCR product is no longer than about 3000 nucleotides. The upper limit of test nucleic acid length is dictated by the degree of size resolution of the analysis method used to analyze the cleavage fragments. Generally, longer PCR products ("amplicons") are preferred simply because fewer different PCR reactions are needed to cover a given genetic target thereby reducing the cost of a mutation analysis. The PCR may be applied to genomic DNA or, in the case of RT-PCR, to cDNA generated by applying a reverse transcription reaction to RNA, usually mRNA. For eukaryotic genes, RT-PCR is somewhat preferred over amplification of genomic targets simply because amplicon size can be maximized without concern about exon size. There is some preference to exclude intronic target sequence, except possibly that close to the splice junctions, because the introns are often polymorphic in ways which have no known biological consequence. Such "silent" polymorphisms can act as a background signal in CCM output thereby reducing sensitivity to clinically important mutations which influence the amount and/or structure of mRNA and therefore of expressed protein.

PCR and RT-PCR methods are well known to practitioners of the art of genetic analysis and are therefor in need of little elaboration (Dieffenbach & Dveksler). Preferably, the PCR amplification is optimized such that (1) it generates between about 1 and 100 nM of specific PCR product (enough to see on an ethidium-stained agarose electrophoresis gel using traditional methods), (2) creates negligible misprimed or truncated side products, and (3) results in less primer oligomer than specific PCR product. Hot-Start PCR methods, also well known in the field of mutation detection, often serve to improve amplification specificity and sensitivity, especially when amplification is performed on a small number of target copies, e.g., less than about 1000 molecules, or on long targets. Relatively long annealing and extension times, from 2 to about 6 minutes, also help to minimize truncation product and maximize specific PCR product yield, especially for targets longer than about 1000 nucleotides.

Amplicon is labeled according to the analytical method utilized in the analysis step of the CCM process. Preferred labels include radioactive labels (e.g., $^{32}P$), fluorescent dyes, or a binding moiety which is a member of a binding pair, e.g., biotin, antigen, receptor and the like. Preferably, two different spectrally resolvable dyes are attached to the two primers used to create an amplicon. Then, if the cleavage fragments are analyzed in a multi-color fluorescent nucleic acid fragment analyzer, such as an automated DNA sequencer, the association of fragment size with color unambiguously estimates the position of any mutation in the amplicon. More preferably, the same two dye-tagged primers are used to create both the control nucleic acid (if a control is used) and the test nucleic acid. Finally, with this fragment-tagging strategy, it often is practical and desirable (in the interest of cost reduction) to co-amplify several amplicons of resolvable size. As modern multi-color automated DNA sequencers can simultaneously analyze 4 different dyes and soon will be able to process more than 4 dyes at the same time, different amplicons can use different pairs of dyes to allow unambiguous identification of which multiplexed amplicon generated a given set of fragments. However, even if only two dyes are used, this distinction still can be made by correlating the appearance of cleavage fragments with the loss of full-length amplicon in the analytical electropherogram, as long as every amplicon gives a unique signal.

Several labeling strategies may be used to label the nucleic acids of the invention. In a first method, the 5'-end of the primer is labeled, e.g., by performing the amplification reaction using a labeled primer. Alternatively, the amplicon is internally labeled, e.g., by incorporating labeled dNTP's (mixed with un-tagged dNTP's) during the PCR. Although internal labeling has some advantage with respect to signal strength, especially if multiple mutations are expected in an amplicon, it has several weaknesses in most contexts. Because all fragments created by a cleavage are labeled, it is hard to estimate the position of the mutation in the target sequence, complicating second-tier analysis, especially when amplicons over about 500 nt in length are made. In addition, if the internal labels are dyes or binding moieties, there will be a binomial distribution of amplicons bearing different numbers of labels. Because such label molecules affect electrophoretic mobility, such heterogeneous internal labeling broadens peaks, reducing sensitivity and resolution. Finally, internal labeling results in large differences in signal strength between large and small fragments, complicating development of a method which detects all fragments with comparable sensitivity.

In one alternative aspect of the present invention wherein hydroxylamine is used in place of permanganate ion in the base-removal reaction (see below), it is necessary to replace the customary thymines in the nucleic acid sample with uracils. This change, accomplished by replacing dTTP completely with dUTP in the PCR used to generate the test nucleic acid and any control nucleic acid which is used, may reduce PCR yield by as much as an order of magnitude. Effective remedies to restore PCR efficiency include (a) increasing the dUTP concentration by a factor of 2 to 5, and (b) increasing the annealing or extension times by several minutes. Inclusion of betaine in the PCR, at a concentration of about 1M to 3M, also may counteract the mild inhibition of PCR by dUTP. This change may require a reduction in the annealing or extension temperatures by up to about 5° C. in order to restore amplification efficiency.

III. HETERODUPLEX FORMATION

There are two preferred methods suitable for generating the heteroduplex nucleic acid of the present invention. In a first method, the nucleic acid sample is composed of a control nucleic acid and a test nucleic acid from the individual or tissue suspected of carrying mutations. This first approach is required to identify mutations for which the test sample is homozygous or otherwise genetically uniform (as, for example, results from oncogenic loss of heterozygosity). In an alternative method, no control nucleic acid is included and only a target nucleic acid is used in the heteroduplex formation reaction. Thus, in the second method, heteroduplex is formed simply by subjecting the test nucleic acid to denaturation and renaturation, as described above. This second approach suffices if the test sample is heterozygous for the mutation of interest or if the source of the test sample is a tissue, such as a tumor or a precancerous lesion, containing both normal and oncogenically mutated cells.

Whether using the first or second heteroduplex formation method, the general steps of the method are as follows. The nucleic acid sample is denatured briefly to create single-stranded nucleic acid, and it then is allowed to renature to regenerate duplex DNA in which the two strands from the test nucleic acid (and control nucleic acid if present) have reassociated in a random manner. Denaturation/renaturation most conveniently is performed by heating the mixture to a temperature between about 90° C. and 100° C., holding the mixture at the higher temperature for only a few seconds (to minimize potential damage to the nucleic acid), and then returning the temperature to a value between about 4° C. and 25° C. A time- and temperature-programmable thermal cycler, such as is used to control the PCR, is a preferred apparatus for completing the heteroduplex formation operation.

IV. BASE-REMOVAL REACTION

In an important aspect of the present invention, base removal is effected using a reagent including permanganate ion, e.g., $KMnO_4$. This reaction occurs optimally at a temperature between about 0° C. and about 50° C., for times between about 5 min and about 30 min, at final permanganate concentrations of between about 0.1 mM and about 10 mM, buffered at a pH in the range of 6 to 9, e.g., by a mixture of ammonia and ammonium sulfate (above about pH 8.25) or by a phosphate salt (below about pH 8.25). Because of the way that time, temperature, pH, and permanganate ion concentration contribute to reaction rate, there are many possible combinations of these variables with comparable base-removal efficiency. Shorter times, down to about 5 min, are preferable in order to minimize total analysis time, however times substantially shorter than 5 minutes are undesirable because the reaction becomes more difficult to control reproducibly. Higher temperatures are preferred because they offer a simple way to control reaction completeness, i.e., the base-removal reaction can be effectively stopped by returning the temperature to the range of 0° C. to 25° C. For example, the base-removal reaction can be controlled by adding a small volume, perhaps a few microliters, of a 1 to 10 mM $KMnO_4$ stock solution to a 10 to 100 µl volume of denatured/renatured DNA in PCR buffer at 4° C. in a 500 microliter microfuge tube, raising the temperature to 50° C. in a DNA thermal cycler and holding it there for 5 minutes, and then returning the temperature rapidly to 4° C. Base-removal temperatures above about 50° C. are risky because they might lead to sufficient local denaturation of perfectly matched AT-rich sequences to yield unacceptable false positive results. $KMnO_4$ treatment of PCR reaction mixtures will oxidize residual untreated dNTP's and primers, thereby reducing the amount of $KMnO_4$ available to react with mismatched bases. This side reaction can be minimized by designing the PCR to employ the lowest practical dNTP concentrations, on the order of 10 µM, and in any case below about 100 µM. A pH9 buffer consisting of a mixture of ammonia and ammonium sulfate is especially effective for PCR, instead of the Tris buffer commonly used for PCR.

Optimization of base removal by permanganate ion treatment has several goals: (1) maximize removal of mismatched T's (the easiest target for permanganate ion), (2) maximize removal of mismatched C's (a harder target for permanganate ion), and (3) minimize removal of any non-mismatched nucleotides in the heteroduplex nucleic acid. Certain control reactions are useful for monitoring the performance of the base-removal reaction and identifying optimal reaction conditions: (1) a normal control (preferably one with an AT-rich subdomain), containing no heteroduplex, (2) an originally heterozygous sample carrying a TA to AT transversion, and (3) an originally heterozygous sample containing a CG to GC transversion. [The background reaction also can be monitored at non-mutated positions in the two transversion samples.]

In a preferred embodiment of the present invention, the reagent used to effect the base-removal reaction includes, in addition to permanganate ion, a high concentration, e.g., 1 to 5 M, of either a tetraalkylammonium (preferably tetramethylammonium) salt or betaine (a neutral, zwitterionic, tetramethylammonium analogue). These additives serve to enhance base-removal efficiency and specificity, and, by stabilizing AT-rich duplex nucleic acid, permit the use of higher base-removal temperatures (for enhanced control, as described above) without increasing false positive signals.

Betaine is the most preferred alternative because it contributes nothing to the ionic strength of the reaction mixture and therefore does not have to be removed from the reaction product prior to conducting the cleavage reaction and subsequent analysis of the processed heteroduplex. Betaine is soluble in water up to about 5 M. Working betaine concentrations as high as 2 to 3 M are attained easily by mixing a 5 M betaine stock solution, possibly containing diluted permanganate ion, with approximately an equal volume of the nucleic acid sample. However, a preferred way to reach a high betaine concentration in the base-removal reaction is to perform the PCR (used to generate the test and control nucleic acids) directly in 2 to 3 M betaine. In addition to facilitating the CCM reaction, this modification of conventional PCR conditions often improves PCR specificity and does not reduce amplification efficiency if the annealing and extension temperatures are reduced from otherwise optimal values by a few Celsius. Modest increases in PCR annealing and extension times are also desired when including betaine in the PCR. Betaine is capable of reducing $KMnO_4$, thereby reducing the effectiveness of the latter reagent for mismatched base removal. Therefor $KMnO_4$ oxidation in the presence of betaine preferably is conducted at a temperature below about 25° C.

If a tetraalkyammonium salt is added to the base-removal reaction instead of betaine, it preferably is not included in the PCR in the high concentration range needed to benefit the base-removal reaction. Therefore the tetraalkylammonium salt is preferably added after completion of the PCR from a concentrated stock solution, which also may serve as the permanganate ion stock solution, typically by diluting the DNA, already in a PCR buffer, approximately 50% with the stock reagent. Preferred tetraalkylammonium salt anions include chloride, fluoride, hydrogen sulfate, sulfate, nitrate, silicate, and tetrafluoroborate (Aldrich Fine Chemicals, Milwaukee, WIS.).

When tetraalkylammonium salt is used in the base-removal reaction, its concentration must be substantially reduced (by at least 90 to 99%) before subjecting the base-removal product to a cleavage reaction. While ethanol precipitation may be used to remove the tetraalkylammonium salt, in the present invention, alternative desalting methods are preferred which are faster, require less rigorous temperature control, more reliably give high recovery, and require less operator skill. In one preferred desalting method the base-removal reaction product is filtered using a diafilter having a membrane which substantially retains duplex DNA larger than about 50 base pairs and passes smaller molecules. An additional benefit of diafiltration is that the membrane also passes tagged PCR primers, thereby reducing the low-molecular-weight background in the CCM analysis step. In practice, small-volume diafiltration such as this can be performed by diluting the sample 10- to 100-fold with water and applying relatively low gas pressure to the diluted sample above or vacuum to the space below a diafiltration membrane mounted in a pressure/vacuum manifold (or in a microtiter plate mounted in a vacuum manifold). However, preferably diafiltration is performed by placing the diluted base-removal reaction mixture in a spin-filtration microconcentrator and centrifuging at low speed (less than about 5000 rcf) in an angle-head microcentrifuge for the period of time, commonly less than about 10 minutes, needed to return the volume to a value 50 to 100% as large as the undiluted sample volume. A suitable commercially available device is the disposable Pall Filtron (Northborough, MASS.) NANOSEP™ 30K Microconcentrator, though the NANOSEP™ 10K device also works. In a preferred technique for minimizing sample-handling steps all CCM chemical processing steps are performed in the sample reservoir of such a centrifugal microconcentrator, as the membrane in the bottom passes negligible fluid without the application of pressure and the sample reservoir cap minimizes evaporative loss.

In an alternative desalting method the base-removal reaction mixture is contacted with a small volume of a beaded mixed-bed ion exchange or ion-retardation resin, such as AG501-X8, Bio-Rex MSZ501(D), or AG11 A8, from Bio-Rad Laboratories (Hercules, CALIF.). The minimum wet capacities of these resins (0.7 to 1.5 meq/mL) are such that on the order of 200 to 500 μL of resin are needed to desalt 100 μL of 3 M tetraalkylammonium salt, and the resin size exclusion limit, about 1000 daltons, assures that analytically important nucleic acid is not captured inside the beads.

In an additional embodiment of the present invention, cytidine removal during the base-removal reaction is facilitated by addition of an effective amount of hydroxylamine to the permanganate base-removal reagent. Comparable hydroxylamine treatment conditions are used, whether betaine or a tetraalkylammonium salt is present. In contrast to conventional hydroxylamine treatment in CCM, the hydroxylamine stock solution is prepared from the free base (commercially available as a 50% aqueous solution) rather than the hydrochloride salt, pH-adjusted with acid to the highest pH, on the order of 8 to 10, consistent with complete avoidance of duplex nucleic acid denaturation. Such an approach minimizes the contribution of hydroxylamine to the ionic strength, so that if hydroxylamine treatment is performed in the presence of betaine instead of a tetraalkylammonium salt, a desalting step is not needed before cleavage and subsequent analysis. The minimum hydroxylamine concentration is used which is effective for mismatched cytidine cleavage. To minimize the required hydroxylamine concentration, the highest practical reaction temperature, e.g., approximately 50° C., and the longest practical reaction time, e.g., 30 to 60 minutes, are used.

In an alternative aspect of the present invention, base removal is accomplished using hydroxylamine in place of permanganate ion. In this aspect, the nucleic acid sample is prepared with complete replacement of thymine by uracil. The principal condition applied to the hydroxylamine treatment is that the pH must be high enough, preferably above approximately pH 9, to favor ionization of mismatched uracils, yet low enough, preferably below approximately pH 10.5, not to destabilize correctly matched duplex nucleic acid. The inclusion of about 1 M to 3 M betaine, tetramethylammonium salt, or tetraethylammonium salt in the base-removal reaction helps to stabilize duplex nucleic acid, thereby raising the maximum tolerated pH. Should a tetraalkylammonium salt be used, it is removed, e.g. by diafiltration, before cleavage of abasic sites as described above. Betaine is preferred for duplex nucleic acid stabilization, not only because it avoids the need for desalting, but also because its nonionic nature favors the base-removal reaction.

V. CLEAVAGE REACTION

After completion of the base-removal reaction, the heteroduplex nucleic acid is subjected to a cleavage reaction which causes the cleavage of the heteroduplex at any abasic site, i.e., nucleotide positions at which a base has been removed. According to the present invention, the cleavage reaction is effected by incubating the heteroduplex with a 1,2-diamine, e.g., 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, or trans-1,2,-diaminocyclohexane.

Preferably, the cleavage reaction is conducted at a 1,2-diamine concentration in the range of about 10 to 100 mM, at a pH of about 5 to about 9, at a temperature of about 25° C. to about 40° C., for an elapsed time between about 10 minutes and one hour. Also preferably, the cleavage reaction contains a nucleic acid denaturant, such as 2-pyrrolidinone or urea, at a concentration in the range of about 1 M to 10 M. The exact combination of conditions depends on which cleavage reagent is used and what combination of reagents and solvents was used in the base-removal reaction.

If the base-removal reagent is not removed by desalting, preferably the temperature of the cleavage reaction is at least 10° C. lower than that used in the base-removal reaction. This lower reaction temperature is desirable in order to minimize the activity of any residual base-removal reagent (in order to minimize base removal at non-mismatched sites).

If hydroxylamine is used for base removal and is not removed by a desalting step prior to conducting the cleavage reaction, residual hydroxylamine activity may be reduced by conducting the cleavage reaction at a pH in the 5–6 range and using a cleavage reagent which maintains an unprotonated amino group in that pH range, e.g., diethylenetriamine, triethylenetetraamine, cis-1,2-diaminocyclohexane, or trans-1,2,-diaminocyclohexane. If a tetraalkylammonium salt is used during base removal, then desalting, as described above, is done prior to conducting the cleavage reaction, and the preferred desalting buffer is used instead of water to dilute the sample before desalting. If betaine and hydroxylamine are used during base removal, the need for desalting depends on whether hydroxylamine adds enough ionic strength to interfere with the post-cleavage separation step. If betaine and no hydroxylamine is used during the base-removal reaction, no desalting is done before adding the cleavage reagent to the nucleic acid. Preferably, a cleavage reagent stock solution is prepared which is 10 to 100 times more concentrated than is desired for the actual cleavage reaction. This stock is pH-adjusted so that after dilution into the nucleic acid sample, the desired final pH is attained.

Regardless of the particular chemistry used to effect the base removal and cleavage reactions, subsequent to the cleavage reaction the cleavage product is in a suitable condition to be analyzed under denaturing conditions without further separation steps to remove residual reagents. Preferably, in order to minimize the activity of residual reagents which might create a background signal unrelated to the presence of mutations, the cleavage product is incubated at 0° C.–4° C. subsequent to the cleavage reaction and prior to analysis.

VI. ANALYSIS OF CLEAVED HETERODUPLEX

Any method which can identify the presence of and location of heteroduplex cleavage by fragment size or otherwise may be used to analyze the cleavage products of the present invention. One preferred analytical method is denaturing electrophoresis using a "sequencing gel" or in a capillary containing entangled polymer using a detection system including a multicolor fluorescent detector, e.g., the Model 373A (slab gel), Model 377 (slab gel), or Model 310 (capillary) sequencer from Applied Biosystems (Foster City, CALIF.). Analysis is performed according to instructions provided by Applied Biosystems for GeneScan™ fragment analysis. These instructions define the electrophoresis loading reagent (a mixture of a DNA denaturant, a chelator, and a loading dye, usually augmented with fluorescent size-standard fragments) into which the cleavage product is diluted, the methods of preparing and loading the electrophoresis medium, the method of running the electrophoresis with real-time fluorescent detection, and the method of analyzing the resulting electropherograms to determine which fragment sizes were produced with which dye tag.

Alternatively, cleavage products may be analyzed in only a few minutes by anion-exchange HPLC, as described by the present inventor in European Patent Application No. 0 507 591 A2, (1992). The resolution and size range of this separation can be adjusted to the desired performance level by computer control of the length and steepness of the salt elution gradient. Furthermore, automated fraction collection of fragments, using standard equipment and procedures, can supply material for direct sequence analysis to confirm the exact nature of a mutation.

Regardless of the nature of the mutation, e.g., base substitution, insertion, or deletion, heteroduplex generation results in two heteroduplex molecules and regenerates the two parental homoduplex molecules (normal and mutant), because there are four ways that the two plus strands (normal and mutant) and the two minus strands (normal and mutant) of a denatured mixture of normal and mutant duplex nucleic acid molecules can recombine. At each mutated position, there is a mismatched pyrimidine/purine, pyrimidine/pyrimidine or purine/purine base pair in each heteroduplex molecule. CCM chemistry cleaves primarily, though not always completely, at mismatched pyrimidines. Therefore, because there are two heteroduplex molecules for each mutated position, a total of four single-stranded cleavage fragments are formed. As long as the CCM process uses base-removal chemistry which cleaves at all mismatched pyrimidines and as long as the labeling technique used employs distinguishable labels for each of the two primers responsible for any amplicon, every mutation results in two tagged cleavage fragments in one or two colors (in the case of a base substitution, depending on whether it is a transition or transversion). The relationships between fragment color and size determine unambiguously the approximate position of the mutation in the amplicon. The two tagged peaks in the analytical output (e.g., electropherogram) may not be of similar strength, because base-removal efficiency depends on sequence context.

VII. EXAMPLES

The invention will be further clarified by a consideration of the following prophetic examples, such examples being intended to be purely exemplary of the invention and not to in any way limit its scope.

EXAMPLE 1

DNA is purified by methods well known to molecular biologists, from two immortalized cell lines from the Coriell Human Genetic Mutant Cell Repository (Camden, N.J.). Cell line # GM12785 is a compound heterozygote for two cystic fibrosis (CF) mutations (in the CFTR gene): R347P (a G-to-C transversion at cDNA nucleotide position 1172 in exon 7) and G551D (a G-to-A transition at cDNA nucleotide position 1784 in exon 11). Cell line # GM11282 is also a CF compound heterozygote: mutations 621+1G/T (a G-to-T transversion at the first intronic nucleotide downstream from cDNA nucleotide position 621, just beyond the end of exon 4) and G85E (a G-to-A transition at cDNA nucleotide position 386 in exon 3). Because all four mutations are heterozygous, an approximately equimolar mixture of normal and mutant DNA is created for a mutation whenever primers specific for one of the two mutated exons is used to amplify any one of the DNA samples. Four primer pairs are used in this example, as summarized in Table I.

TABLE I

CFTR Exonic Primer Pairs

| Exon | Strand | Primer Name | Primer Sequence | 5" Dye Tag |
|---|---|---|---|---|
| 3 | plus | CF001 | CCCTGGGATAGAGAGCTGGCT | FAM |
|   | minus | CF002 | CCCTGATACATAATGAATGTACAAATGAG | TET |
| 4 | plus | CF003 | CCCGGAAGAATCATAGCTTCCTATG | FAM |
|   | minus | CF004 | CCCAACATGTACGATACAGAATATATGTG | HEX |

TABLE I-continued

CFTR Exonic Primer Pairs

| Exon | Strand | Primer Name | Primer Sequence | 5" Dye Tag |
|------|--------|-------------|-----------------|------------|
| 7 | plus | CF007 | CCCGAAGGCAGCCTATGTGAG | FAM |
|   | minus | CF008 | CCCGTTTGTACAGCCCAGGG | TET |
| 11 | plus | CF011 | CCCCCTTTCAAATTCAGATTGAG | FAM |
|    | minus | CF012 | CCGAATGACATTTACAGCAAATG | HEX |

A total of 8 PCR's are performed. Each DNA sample is amplified with each of the four primer pairs of Table I. Table II summarizes the DNA fragments expected to be seen if the denatured/renatured PCR products are subjected to CCM in which cleavage occurs only at mismatched pyrimidines in the heteroduplexes and the cleavage products are analyzed on a multicolor fluorescent automated DNA sequencer.

TABLE II

Predicted CCM Fluorescent Fragment Patterns

| Source DNA | Primers | Parental Fragments | Cleavage Fragments |
|------------|---------|--------------------|--------------------|
| GM11282 | CF001/002 | 139nt (FAM,TET) | 53nt (FAM,TET) |
|  | CF003/004 | 237nt (FAM,HEX) | 183nt (FAM), 53nt (HEX) |
|  | CF007/008 | 189nt (FAM,TET) | none |
|  | CF011/012 | 206nt (FAM,HEX) | none |
| GM12785 | CF001/002 | 139nt (FAM,TET) | none |
|  | CF003/004 | 237nt (FAM,HEX) | none |
|  | CF007/008 | 189nt (FAM,TET) | 149nt (FAM), 39nt (TET) |
|  | CF011/012 | 206nt (FAM,HEX) | 76nt (FAM,HEX) |

A wax-mediated Hot Start PCR is performed according to the following design. A bottom reaction mixture is prepared, consisting of 40 $\mu$M of each of the four standard dNTP's, 0.05% Triton X-100, and 0.1 units/$\mu$L of AmpliTaq® DNA polymerase (Perkin Elmer-Applied Biosystems, Foster City, CALIF.). For each PCR, 10 $\mu$L of bottom reaction mixture is added to the bottom of a MicroAmp™ reaction tube (PE-Applied Biosystems); one PCR Gem-50™ (PE-Applied Biosystems) is added to each tube, which then is closed and heated to 70° C. for 3 min in a GeneAmp™ PCR System 9600 thermal cycler (PE-Applied Biosystems) to layer the wax. When the tube has returned to room temperature, over the wax is placed 10 $\mu$L of a top reaction mixture consisting of 40 mM ammonium sulfate adjusted to pH 9.3 with ammonia, 2.7 mM magnesium sulfate, 4 M betaine, 100 genome copies (0.6 ng) of the desired purified human genomic DNA, and two primers (specific for the exon targeted) each at a concentration of 0.5 $\mu$M. Amplification is performed in the same thermal cycler by running 3 cycles, at the fastest possible ramp rates, with the following settings: 98° C. for 5 seconds, 55° C. for 6 minutes, 70° C. for 2 minutes; then 26 cycles with the following settings: 94° C. for 5 seconds, 55° C. for 6 minutes, 70° C. for 2 minutes. Then the polymerase is inactivated and heteroduplex is formed by heating at 99.9° C. for 20 minutes, followed by rapid cooling to room temperature (fastest possible ramp rate). This step can be programmed to occur immediately after the last PCR cycle rather than as a separate operation. [The polymerase should be inactivated before heteroduplex formation to assure that primer extension does not compete with heteroduplex formation. If the prolonged heating is undesirable, e.g., because the DNA is labile under these conditions, enzyme can be inactivated by adding disodium EDTA to a final concentration of 5 mM between the end of the PCR and a much milder denaturation/renaturation step, such as heating to 95° C. for 15 seconds before return to room temperature.]

In order to achieve mismatched thymine and cytidine removal from the heteroduplex formed by the preceding operations, each 20 $\mu$L reaction volume is mixed with 5 $\mu$L of 5 mM $KMnO_4$ in water and incubated at 50° C. for 5 min in a thermal cycler before rapid cooling to room temperature. In order to effect cleavage of abasic sites, each 25 $\mu$L reaction volume is (a) mixed with 20 $\mu$L of 2-pyrrolidinone and 5 $\mu$L of 400 mM 1,2-ethylenediamine which has been adjusted to pH 8.0 with acetic acid, (b) incubated at 99° C. for 5s, and (c) is incubated at 30° C. for 30 minutes in a thermal cycler before rapid cooling to room temperature. All three of these steps are performed in the same microtube used for PCR and heteroduplex formation.

The cleavage products then are subjected to GeneScan™ analysis in a Model 310 automated DNA sequencer (PE-Applied Biosystems) according to the manufacturer's instructions. FAM-tagged fragments are observed in the blue channel of filter set C; TET-tagged fragments are tracked in the green channel; HEX-tagged fragments are tracked in the yellow channel. The red channel is used for a TAMRA-tagged GeneScan™ size-standard cocktail (PE-Applied Biosystems). The terms, FAM, TET, HEX, and TAMRA, refer to a set of spectrally resolved, fluorescent and rhodamine derivatives developed by PE-Applied Biosystems, attached to the primer 5' ends by chemistries fully described by the manufacturer. The GeneScan™ electropherograms for the eight different PCR products subjected to the CCM process just described show parental and cleavage-product peaks at approximately the sizes indicated in Table II, above, and substantially no other peaks except in the size range below about 30 nt. This latter smattering of very small fragments likely arises from low-level primer inhomogeneity, not the existence of mutations, as can be verified by their presence at comparable strength when homozygous normal samples are examined (i.e., the primer and DNA combinations predicted in Table II to have no cleavage fragments).

EXAMPLE 2

PCR, heteroduplex formation, mismatched base removal, abasic site cleavage, and GeneScan analysis are performed as in Example 1 except for the following changes: (1) betaine is omitted from the PCR top reaction mixture; (2) annealing temperatures in the PCR thermal cycles are increased from 55° C. to 59° C.; (3) for the first stage of mismatched base removal (thymine removal), the 20 $\mu$L of denaturation/renaturation product is mixed with 10 $\mu$L of 1.2 mM KMnO$_4$ 6M TMAC and incubated at 50° C. for 5 minutes before rapid cooling to room temperature; (4) (a new step) for mismatched cytidine removal, 5 μL of 1M hydroxylamine, adjusted to pH8.5 with acetic acid, are added to the 30 μL of thymine-removal product, which then is incubated at 50° C. for 15 minutes before rapid cooling to room temperature; (5) (a new step) the entire product (35 μL) from the cytidine-removal step is mixed with 465 μL water, added to the sample reservoir of a NANOSEP™ 30K microconcentrator (Pall Filtron, Northborough, MASS.) and centrifuged at room temperature in an angle-head rotor at 4000 rcf until the volume has been reduced to about 10 μL and the total volume is restored to 25 μL with water before addition of 2-pyrrolidinone and ethylenediamine, as above.

Abasic site cleavage and GeneScan analysis are performed as described in Example 1. The results are substantially as described in Example 1.

EXAMPLE 3

PCR, heteroduplex formation, mismatched base removal, abasic site cleavage, and GeneScan analysis are performed as in Example 1 except for the following changes: (1) for the first stage of mismatched base removal (thymine removal), the 20 μL of denaturation/renaturation product are mixed with 5 μL of 2.0 mM KMnO$_4$ and incubated at 50° C. for 5 minutes before rapid cooling to room temperature; (2) (a new step) For mismatched cytidine removal, 4 μL of 1M hydroxylamine, adjusted to pH 8.5 with acetic acid, are added to the 25 μL of thymine-removal product, which then is incubated at 50° C. for 15 minutes before rapid cooling to room temperature; (3) for abasic site cleavage, 23 μL of 2-pyrrolidinone and 6 μL of 400 mM 1,2-ethylenediamine which has been adjusted to pH 8.0 with acetic acid are added to the 29 μL of cytosine-removal product.

The balance of the abasic site cleavage process and GeneScan analysis are performed as described in Example 1. The results are substantially as described in Example 1.

EXAMPLE 4

PCR, heteroduplex formation, mismatched base removal, abasic site cleavage, and GeneScan analysis are performed as in Example 1 except for the following changes: (1) betaine is omitted from the PCR top reaction mixture; (2) annealing temperatures in the PCR thermal cycles are increased from 55° C. to 59° C.; (3) For mismatched base removal (thymine and cytidine removal), the 20 μL of denaturation/renaturation product are mixed with 10 μL of 3.0 mM KMnO$_4$ 6M TMAC and incubated at 50° C. for 5 minutes before rapid cooling to room temperature; (4) (a new step) the entire product (25 μL) from the mismatched pyrimidine-removal step is mixed with 475 μL water, added to the sample reservoir of a NANOSEP™ 30K microconcentrator (Pall Filtron, Northborough, MASS.) and centrifuged at room temperature in an angle-head rotor at 4000 rcf until the volume has been reduced to about 10 μL. The total volume is restored to 25 μL with water before addition of 2-pyrrolidinone and ethylenediamine, as above.

Abasic site cleavage and GeneScan analysis are performed as described in Example 1. The results are substantially as described in Example 1.

EXAMPLE 5

PCR, heteroduplex formation, mismatched base removal, abasic site cleavage, and GeneScan analysis are performed as in Example 1 except for the following changes: (1) dTTP in the PCR bottom reaction mixture is completely replaced by 200 μM dUTP; (2) the duration of the PCR annealing step (at 55° C.) is increased from 2 to 4 minutes in all cycles; (3) mismatched base removal by KMnO$_4$ is omitted, and instead, the 20 μL of heteroduplex is mixed with 5 μL of unbuffered 2M hydroxylamine and incubated at 50° C. for 30 minutes before rapid cooling to room temperature; (4) the 400 mM 1,2-ethylenediamine stock solution is adjusted to pH 5.0 instead of pH 8.0 before addition to the base-removal product. The results are substantially as described in Example 1.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in these preferred embodiments without departing from the teachings thereof. All such modifications are intended to be encompassed within the following claims.

I claim:

1. A mutation detection method comprising the steps of:
   denaturing a nucleic acid sample, the nucleic acid sample comprising a test nucleic acid;
   reannealing the nucleic acid sample to form a heteroduplex nucleic acid;
   performing a base-removal reaction by reacting the heteroduplex nucleic acid with permanganate ion;
   denaturing the heteroduplex nucleic acid subsequent to the base-removal reaction, thereby forming a denatured heteroduplex nucleic acid;
   performing a cleavage reaction by reacting the denatured heteroduplex nucleic acid with 1,2-diamine, thereby forming a cleaved heteroduplex nucleic acid; and
   analyzing the cleaved heteroduplex nucleic acid to determine whether and at what location cleavage has occurred.

2. The method of claim 1 wherein the nucleic acid sample further includes a control nucleic acid.

3. The method of claim 1 wherein the 1,2-diamine is selected from the group consisting of 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, or trans-1,2,-diaminocyclohexane.

4. The method of claim 3 wherein the 1,2-diamine is selected from the group consisting of diethylenetriamine, triethylamine tetraamine, cis-1,2-diaminocyclohexane, trans-1,2,-diaminocyclohexane, 1,2-diaminopropane, and 1,2-diamino-2-methylpropane.

5. The method of claim 1 wherein the base-removal reaction is performed in the presence of betaine.

6. The method of claim 5 wherein the betaine is present at a concentration of between about 1 M and about 5 M.

7. The method of claim 5 wherein the base-removal reaction further includes reacting the heteroduplex nucleic acid with hydroxylamine.

8. The method of claim 1 wherein the base-removal reaction is performed in the presence of tetramethylammonium salt.

9. The method of claim 8 wherein the tetramethylammonium salt is present at a concentration of between about 1 M and about 5 M.

10. The method of claim 8 wherein the base-removal reaction further includes reacting the heteroduplex nucleic acid with hydroxylamine.

11. The method of claim 8 wherein the tetramethylammonium salt contains an anion selected from the group consisting of bromide, chloride, fluoride, hydrogen sulfate, sulfate, nitrate, acetate, formate, hydrogen phthalate, silicate, and tetrafluoroborate.

12. The method of claim 8 wherein the heteroduplex nucleic acid is desalted subsequent to the base-removal reaction and prior to the cleavage reaction.

13. The method of claim 12 wherein the heteroduplex nucleic acid is desalted by diafiltration.

14. The method of claim 13 wherein the diafiltration is performed using a membrane with an effective size cutoff below about 50 base pairs of duplex DNA.

15. The method of claim 1 wherein the base-removal reaction further includes reacting the heteroduplex nucleic acid with hydroxylamine.

16. The method of claim 1 wherein the step of analyzing the cleaved heteroduplex nucleic acid comprises an analytical separation.

17. The method of claim 16 wherein the analytical separation is electrophoresis.

18. The method of claim 17 wherein the electrophoresis takes place in a medium which denatures the nucleic acid.

19. The method of claim 16 wherein the analytical separation is HPLC.

20. The method of claim 1 wherein the heteroduplex is labeled.

21. The method of claim 20 wherein the label is a fluorescent label.

22. A composition comprising:
    an aqueous solution of potassium permanganate and betaine;
    wherein the aqueous solution is buffered at a pH of between about 5.5 and about 10.0.

23. The composition of claim 22 wherein the potassium permanganate is present at a concentration of between about 0.05 mM and 10 mM.

24. The composition of claim 22 wherein the betaine is present at a concentration of between about 0.5 M and about 5 M.

25. The composition of claim 22 further comprising a heteroduplex nucleic acid.

26. A kit useful for conducting a mutation screening assay comprising:
    a base-removal reagent comprising a permanganate salt;
    a nucleic acid denaturant; and
    a cleavage reagent comprising a 1,2-diamine solution.

27. The kit of claim 26 wherein the 1,2-diamine is selected from the group consisting of 1,2-ethylenediamine, diethylenetriamine, triethylenetetraamine, piperazine, is N,N'-dimethylethylenediamine, 1,2-diaminopropane, 1,2-diamino-2-methylpropane, cis-1,2-diaminocyclohexane, and trans-1,2,-diaminocyclohexane.

28. The kit of claim 26 further including betaine.

29. The kit of claim 28 wherein the betaine is present at a concentration of between about 1 M and about 5 M.

30. The kit of claim 26 further including a tetramethylammonium salt.

31. The kit of claim 30 wherein the tetramethylammonium salt is present at a concentration of between about 1 M and about 5 M.

32. The kit of claim 30 wherein the tetramethylammonium salt includes an anion selected from the group consisting of chloride, fluoride, hydrogen sulfate, sulfate, nitrate, silicate, and tetrafluoroborate.

33. The kit of claim 26 further including hydroxylamine.

34. The kit of claim 26 further including a control nucleic acid.

35. A mutation detection method comprising the steps of:
    denaturing a nucleic acid sample, the nucleic acid sample comprising a test nucleic acid, wherein substantially all thymine nucleotides in the nucleic acid sample have been replaced with uracil nucleotides;
    reannealing the nucleic acid sample to form a heteroduplex nucleic acid;
    performing a base-removal reaction by reacting the heteroduplex nucleic acid with hydroxylamine;
    denaturing the heteroduplex nucleic acid subsequent to the base-removal reaction, thereby forming a denatured heteroduplex nucleic acid;
    performing a cleavage reaction by reacting the denatured heteroduplex nucleic acid with 1,2-diamine, thereby forming a cleaved heteroduplex nucleic acid; and
    analyzing the cleaved heteroduplex nucleic acid to determine whether and at what location cleavage has occurred.

36. The method of claim 35 wherein the nucleic acid sample further includes a control nucleic acid.

37. The method of claim 35 wherein the 1,2-diamine is selected from the group consisting of 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, or trans-1,2,-diaminocyclohexane.

38. The method of claim 37 wherein the 1,2-diamine is selected from the group consisting of diethylenetriamine, triethylamine tetraamine, cis-1,2-diaminocyclohexane, trans-1,2,-diaminocyclohexane, 1,2-diaminopropane, and 1,2-diamino-2-methylpropane.

39. The method of claim 35 wherein the step of analyzing the cleaved heteroduplex nucleic acid comprises an analytical separation.

40. The method of claim 39 wherein the analytical separation is electrophoresis.

41. The method of claim 40 wherein the electrophoresis takes place in a medium which denatures the nucleic acid.

42. The method of claim 39 wherein the analytical separation is HPLC.

43. The method of claim 35 wherein the heteroduplex is labeled.

44. The method of claim 43 wherein the label is a fluorescent label.

45. A kit useful for conducting a mutation screening assay comprising:
    a base-removal reagent comprising hydroxylamine;
    a nucleic acid denaturant; and
    a cleavage reagent comprising a 1,2-diamine.

46. The kit of claim 45 wherein the 1,2-diamine is selected from the group consisting of 1,2-ethylenediamine, diethylenetriamine, triethylenetetraamine, piperazine, N,N'-dimethylethylenediamine, 1,2-diaminopropane, 1,2-diamino-2-methylpropane, cis-1,2-diaminocyclohexane, and trans-1,2,-diaminocyclohexane.

47. The kit of claim 45 further including betaine.

48. The kit of claim 47 wherein the betaine is present at a concentration of between about 1 M and about 5 M.

49. The kit of claim 45 further including a tetramethylammonium salt.

50. The kit of claim 49 wherein the tetramethylammonium salt is present at a concentration of between about 1 M and about 5 M.

51. The kit of claim 49 wherein the tetramethylammonium salt includes an anion selected from the group consisting of chloride, fluoride, hydrogen sulfate, sulfate, nitrate, silicate, and tetrafluoroborate.

52. The kit of claim 45 further including a control nucleic acid.

* * * * *